United States Patent [19]

Minami

[11] Patent Number: 5,235,360

[45] Date of Patent: Aug. 10, 1993

[54] AUTOMATIC PERIMETER

[75] Inventor: Munehiro Minami, Tokyo, Japan

[73] Assignee: Kabushiki Kaisha TOPCON, Tokyo, Japan

[21] Appl. No.: 766,353

[22] Filed: Sep. 26, 1991

[30] Foreign Application Priority Data

Sep. 27, 1990 [JP] Japan .................................. 2-258649

[51] Int. Cl.$^5$ .............................................. A61B 3/02
[52] U.S. Cl. .................................... 351/226; 351/224; 351/246
[58] Field of Search ................ 351/224, 225, 226, 246

[56] References Cited

U.S. PATENT DOCUMENTS

| | | | |
|---|---|---|---|
| 4,679,920 | 7/1987 | Takashi | 351/226 |
| 5,035,500 | 7/1991 | Rorabaugh | 351/226 |

*Primary Examiner*—Rodney B. Bovernick
*Attorney, Agent, or Firm*—Finnegan, Henderson, Farabow, Garrett & Dunner

[57] ABSTRACT

The present invention discloses an automatic perimeter capable of easily adding or deleting the inspecting points. The present invention includes: target mark exhibiting means exhibiting a target mark at an inspecting point where an exhibiting position is predetermined, in accordance with instructions from instructing means; display means displaying points corresponding, one by one, to the inspecting points which are to be exhibited on the exhibiting means; boundary designating means for designating an adding or deleting area of the inspecting points by drawing a closed curve on the screen of the display means; and exhibiting target mark determining means for determining the inspecting points to be exhibited on the target mark exhibiting means based on the adding or deleting area of the inspecting points determined by the boundary designating means; the instructing means instructing the target mark exhibiting means to exhibit the target marks determined by the exhibiting target mark determining means thereon in an optional order.

17 Claims, 8 Drawing Sheets

AUTOMATIC PERIMETER

BACKGROUND OF THE INVENTION

1. Field of the Invention

This invention relates to an improvement of an automatic perimeter for measuring the visual field by exhibiting a target mark on an inner surface of a dome which constitutes a part of a target mark exhibiting device.

2. Description of the Prior Art

Heretofore, there is known an automatic perimeter for measuring the visual field by exhibiting a target mark on an inner surface of a dome which constitutes a part of target mark exhibiting means. FIG. 11 shows one example of such conventional automatic perimeter. In FIG. 11, the numeral 1 denotes a visual field measuring apparatus body, 2 a housing and 3 a hemispherical dome. A target mark projecting mechanism (not shown) is disposed within the dome 3. A target mark spot light emitting means 4 is disposed on a rear surface side of the dome 3 within the housing 2. The target mark spot light emitting means 4 has a spot light projecting light source. The dome 3 is provided at a front portion thereof with a panel 5. A face portion receiving hole 6 adapted to receive a face portion of a subject is formed in the panel 5. The face portion receiving hole 6 is provided with a face receiving member 7 adapted to fix a face portion. The face receiving member 7 has a forehead contacting portion 8 and a chin receiving portion 9. When testing, the subject places his forehead and chin on the forehead contacting portion 8 and on the chin receiving portion 9, and then inserts his face portion into the face portion receiving hole 6. The subject receives a test by visually confirming an exhibited target mark while fixedly gazing at a fixation mark which is projected on an inner surface 10 of the dome 3. An inspector designates a projecting position, brightness, etc. of a target mark spot projected on the inner surface 10 of the dome 3 by operating various kinds of control switches mounted on instruction means 11 and a light-pen 12.

In an automatic perimeter, when a static visual field measurement is performed, a target mark is usually exhibited on the inner surface 10 of the dome 3 in accordance with a standard inspection pattern (for example, quick screening pattern). However, depending on the results of inspection based on the standard inspection pattern, there are sometimes cases in which a particular area needs to be designated for further detailed inspection. In such a case, a target mark to be exhibited is added or changed. Heretofore, as shown in FIG. 12, a rectangular area 15 is selected as an adding or deleting area of an inspecting point by designating two points on a diagonal line as shown by "X" marks on a display screen 13 of a display device of the instructing means 11. The lattice points 14 within the rectangular area 15 are regarded as inspecting points to be added or deleted, and one or more target mark positions to be exhibited on a target mark exhibiting means by determining the inspecting points. Target marks corresponding, one by one, to the inspecting points are exhibited on the target mark exhibiting means for inspection.

However, in the conventional automatic perimeter, the inspecting points to be added or deleted are limited to those located within the rectangular area 15. Further, a complicated closed curves excluding such inspecting points (for example, inspecting points indicated by "0" marks) which are not intended to be inspected are unable to be designated. Therefore, lattice points which are not intended to be inspected are to be included. Accordingly, a target mark corresponding to an inspecting point which is not intended to be inspected is also automatically exhibited on the target mark exhibiting means, and thus the time required for measuring the visual field becomes unnecessarily long as a whole because target marks corresponding to inspecting points which are not intended to be inspected are automatically exhibited on the target mark exhibiting means. If it is attempted to designate the rectangular area 15 while excluding such inspecting points which are not intended to be tested, the rectangular area 15 must be designated in such a manner as to divide the rectangular area 15 into small portions. Therefore, there is such an inconvenience in that it takes much time for designating an area of inspecting points to be added or to be deleted.

SUMMARY OF THE INVENTION

It is therefore an object of the present invention to provide an automatic perimeter which is capable of obviating the above-mentioned problems.

In order to solve the above-mentioned problems, the present invention is characterized in that it includes:

target mark exhibiting means capable of exhibiting a target mark at an inspecting point where an exhibiting position is predetermined, in accordance with instructions from instructing means;

display means capable of displaying points corresponding, one by one, to the inspecting points which are to be exhibited on said exhibiting means;

boundary designating means for designating an adding or deleting area of the inspecting points by drawing a closed curve on the screen of said display means; and exhibiting target mark determining means for determining the inspecting points to be exhibited on said target mark exhibiting means based on the adding or deleting area of the inspecting points determined by said boundary designating means;

said instructing means instructing said target mark exhibiting means to exhibit the target marks determined by said exhibiting target mark determining means thereon in an optional order.

According to an automatic perimeter of the present invention, the adding or deleting area of the inspecting points is instructed by means of drawing a closed curve on the screen of the display means by the boundary designating means. Then, the exhibiting target mark determining means determines a target mark to be exhibited on the target mark exhibiting means based on the adding or deleting area of the inspecting points. The instructing means instructs the target exhibiting means to exhibit the target marks determined by the exhibiting target mark determining means thereon in an optional order.

DESCRIPTION OF THE PREFERRED EMBODIMENT

Figure 1:
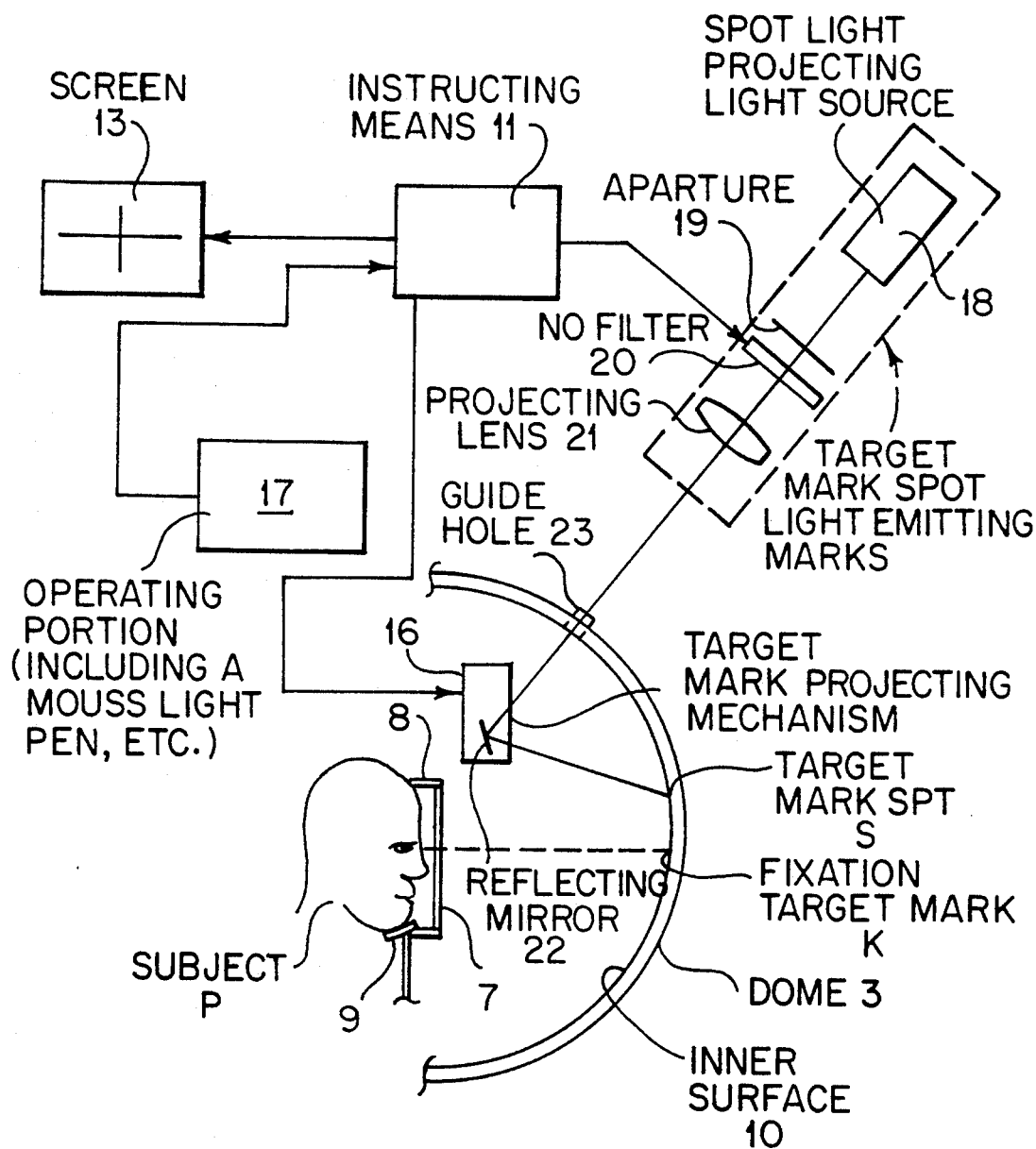
FIG. 1 is a view showing a schematic constitution of an automatic perimeter according to the present invention.
Figure 11:
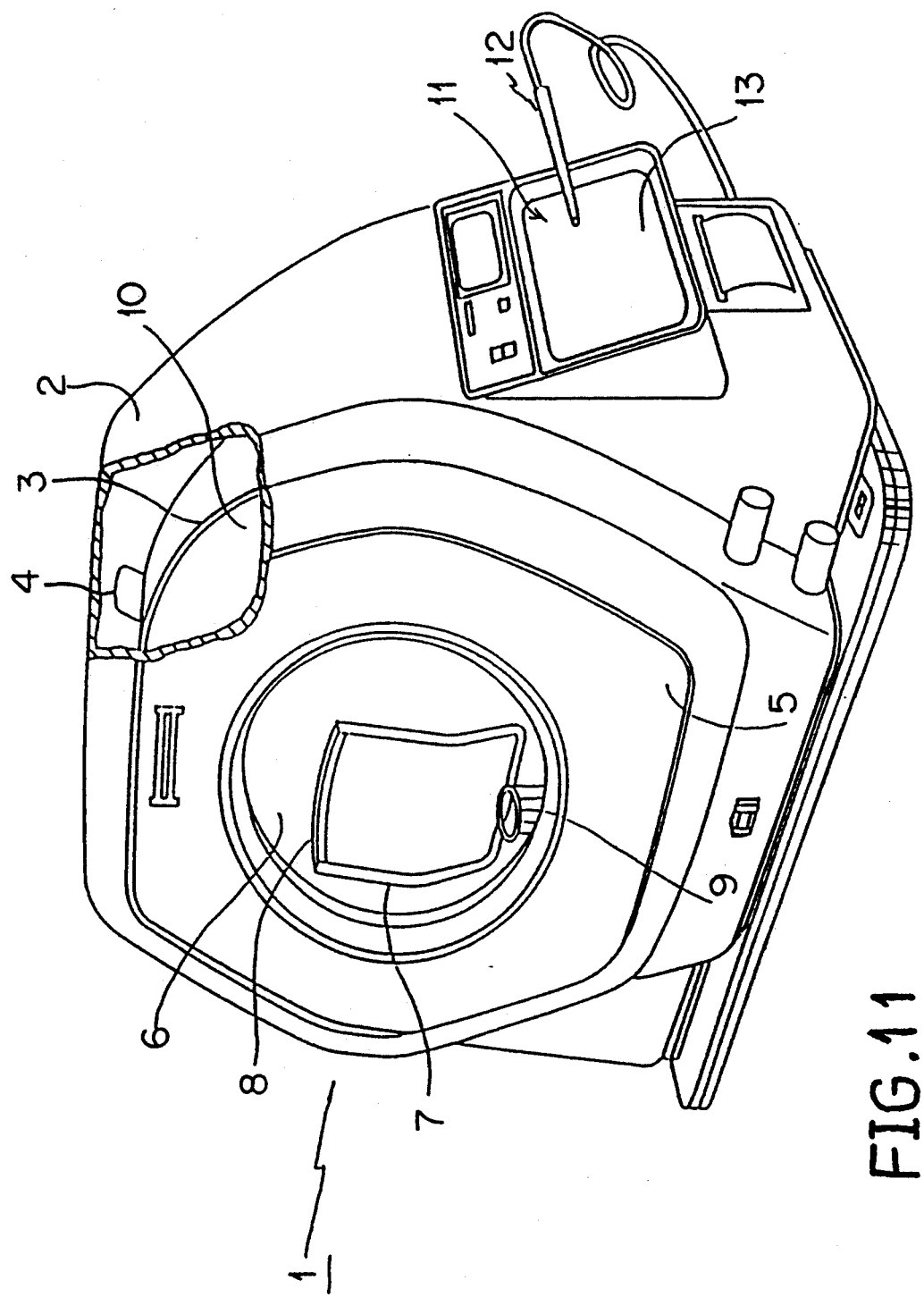
FIG. 11 is a view showing a schematic constitution of the conventional automatic perimeter.
Figure 12:
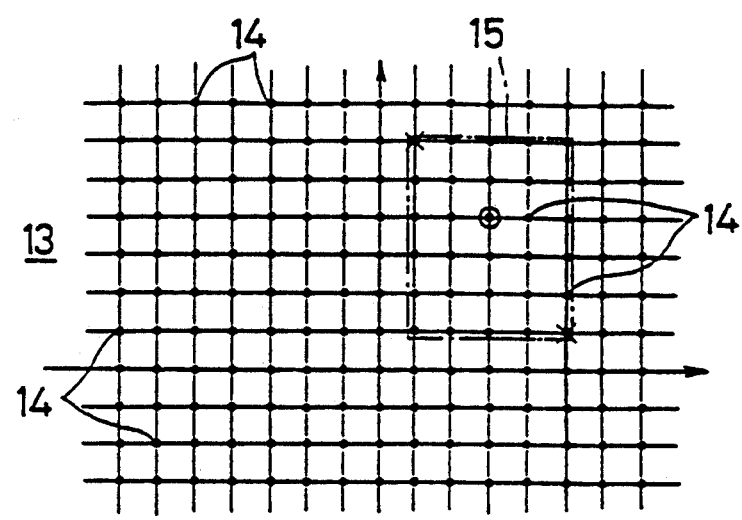
FIG. 12 is a view for explaining one example of designation of an adding or deleting area of the inspecting points in the conventional automatic perimeter.

FIG. 1 depicts a schematic constitution of an automatic perimeter according to the present invention. In FIG. 1, identical component elements with those in the automatic perimeter shown in FIG. 11 are represented by identical reference numerals. An instructing means 11 generally comprises a computer system. The instructing means 11 controls a target mark spot light emitting means 4, a display device having a screen 13, and a target mark projecting mechanism 16. An output from an operating portion 17 which includes a mouse, a light-pen, a track ball, a digitizer, etc. is an input into the instructing means 11. In this embodiment, the operating portion 17 is a mouse. The target mark spot light emitting means 4 generally comprises a spot light projecting light source 18, an aperture 19, an ND filter 20, and a projecting lens 21. The ND filter 20 has a role for setting the brightness of a spot light to a predetermined value. A sequence for a visual field measuring inspection such as, for example, a sequential order for a static inspecting is stored beforehand in the instructing means 11. The target mark projecting mechanism 16 has a reflecting mirror 22. The target mark spot light emitting means 4 emits a target mark spot light from the projecting lens 21 in accordance with the instructions from the instructing means 11. The target mark spot light is guided to the target mark projecting mechanism 16 through a guide hole 23. Then the target mark spot light is reflected by the reflecting mirror 22 and guided to a designated position on an inner surface 10 of a dome 3. By this, a target mark spot S is projected to the designated position on the inner surface 10 of the dome 3. The subject P is measured while fixedly gazing at a fixation target mark K. The fixation target mark K is exhibited on the inner surface 10 of the dome 3 by known means.

Figure 2:
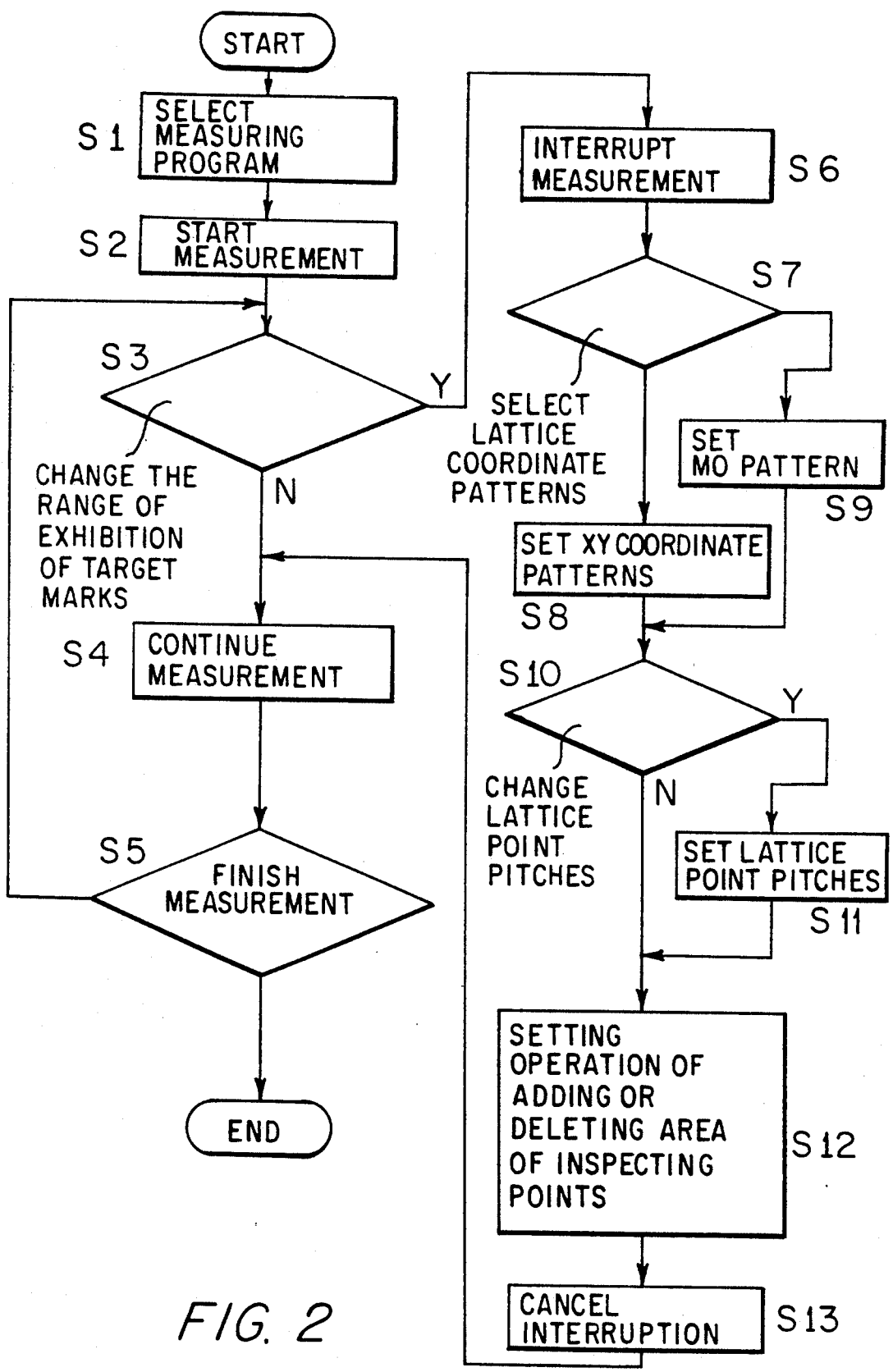
FIG. 2 is a flowchart for explaining the sequential order of measurement for the automatic perimeter according to the present invention.
Figure 3:
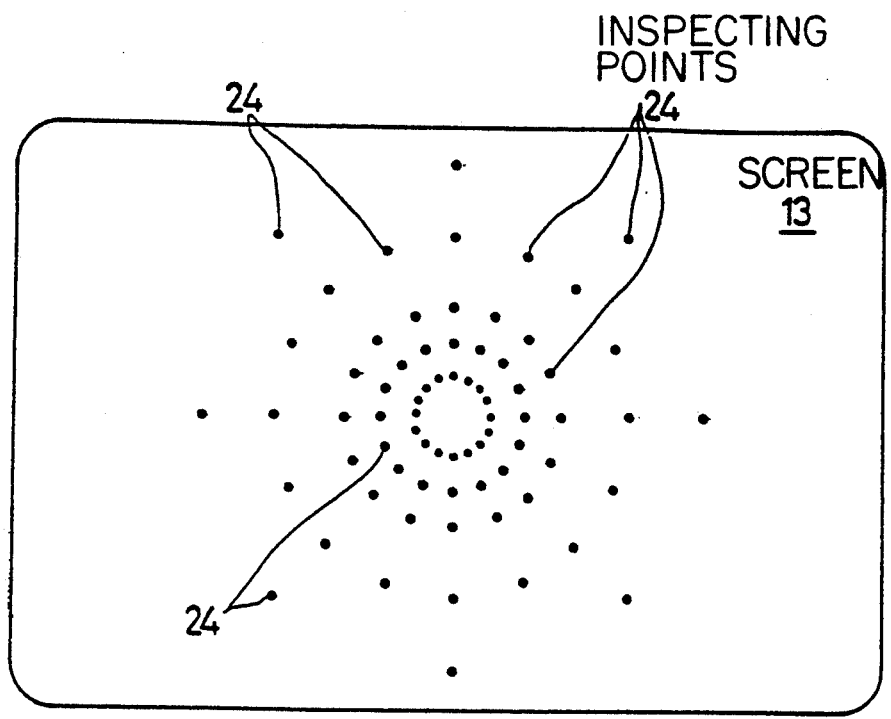
FIGS. 3 and 4 are views showing inspecting points displayed on a screen.
Figure 4:
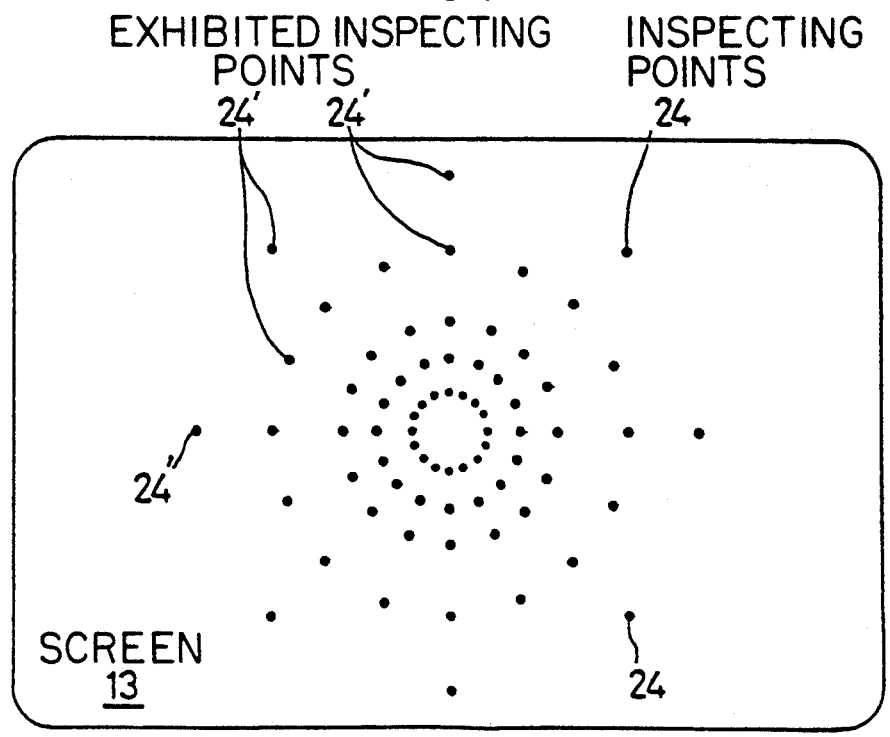

When the operating portion 17 is operated, a program for measurement is selected by computer (S1 of FIG. 2). For example, a quick screening inspection pattern is selected by the mouse. Then, inspecting points 24 are concentrically displayed on the screen 13 of a display device such as liquid crystal, plasma, CRT, etc. as display means based on the quick screening inspection pattern as shown in FIG. 3. These inspecting points 24 also refer to the lattice points corresponding, one by one, to the target marks to be exhibited on the inner surface 10 of the dome 3 constituting a part of the target mark exhibiting means. When the measurement is started (S2), the computer exhibits the target mark S on the inner surface 10 of the dome 3 based on the inspecting points 24. As the target marks S are exhibited one after another, for example, display state of the inspecting points 24 on the screen 13 are changed as indicated by numerals 24' of FIG. 4. For example, the exhibited inspecting points 24' are indicated by "large round black marks" on the screen 13 compared with the inspecting points 24 which have not yet been exhibited. Therefore, the inspector can tell whether the target marks S have already been exhibited or not by seeing the display state of the inspecting points 24.

Figure 5:
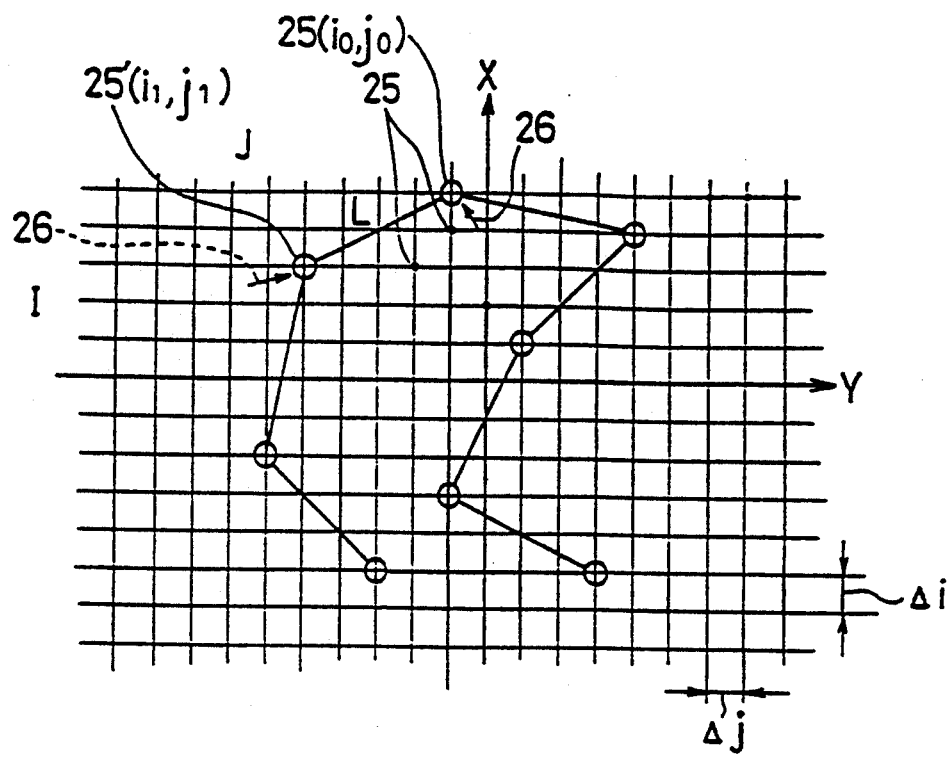
FIGS. 5 and 6 are views showing one example of a coordinate pattern respectively.
Figure 6:
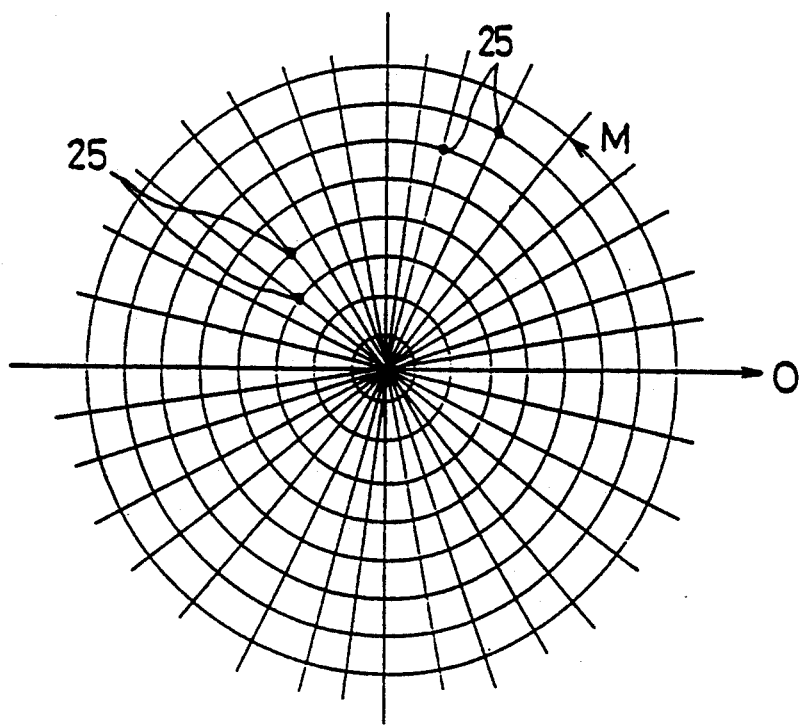

When the exhibiting range of the target marks S is required to be changed midway during the measuring procedure, the mouse is used. When the exhibiting range of the target marks S is not required to be changed, the measurement is simply continued up to the end of the measurement (S3, S4 and S5). In case the exhibiting range of the target marks S is required to be changed, the measurement is temporarily stopped or interrupted (S6) and the inspector selects a lattice coordinate pattern (S7). As the lattice coordinate pattern, an XY coordinate (vertical and horizontal coordinates) pattern where a vertical coordinate line J and a horizontal coordinate line I intersect with each other at right angles as shown in FIG. 5, and an MO coordinate (polar coordinate) pattern where a radial direction coordinate line (offset) O and an angular direction coordinate line (meridian) m intersect with each other at right angles as shown in FIG. 6, are prepared here. These coordinate line are not displayed on the screen 13, and only lattice points as will be described hereinafter are displayed thereon.

In the case of the XY coordinate pattern, a lattice point 25 is defined as a point of intersection between the vertical coordinate line J and the horizontal coordinate line I. On the other hand, in the case of the MO coordinate pattern, another lattice point 25 is defined as a point of intersection between the radial direction coordinate line O and the angular direction coordinate line m. The target marks S are defined in such a manner as to correspond, one by one, to the various lattice points 25. It is presumed here that the XY coordinate pattern is selected (S8). Where the MO coordinate is selected, the procedure of S9 is executed. Then, it is judged whether the pitch of the lattice points 25 should be changed or not (S10). When the pitch of the lattice points 25 should be changed, a pitch changing procedure is executed (S11). If the pitch of the lattice points is set to be small, the maximum number of the target marks to be exhibited is increased, and if the pitch is set to be large, the maximum number is decreased.

Next, an adding or deleting area setting procedure of the inspecting points is executed by designating a closed curve comprising polygonal lines (S12).

Figure 7:
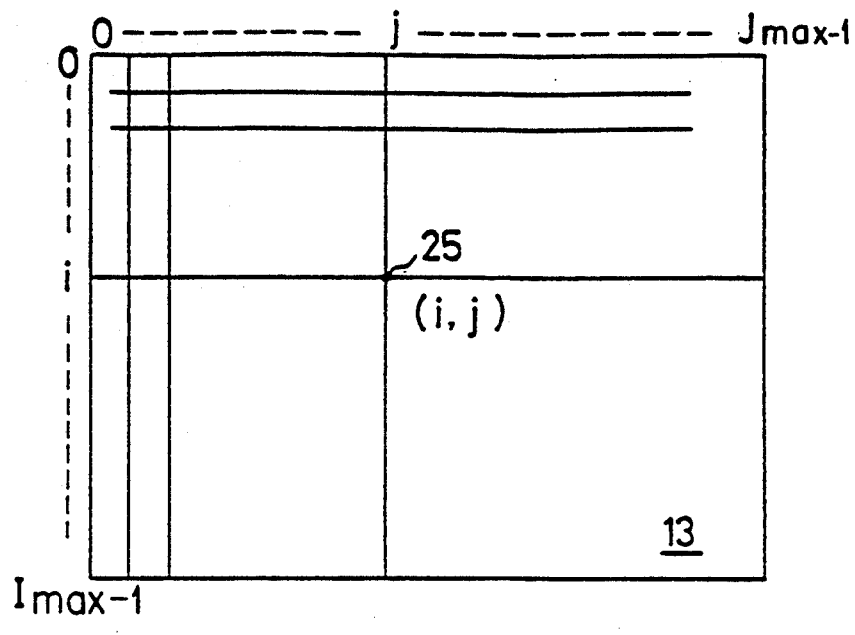
FIG. 7 is a view for explaining the positions of lattice points on the screen.

Locus arrangement memories Li[n] and Lj[n] are prepared in the computer. The locus arrangement memories Li[n] and Lj[n] are memories which are used for drawing polygonal lines. The term "increment n" used herein refers to the number of straight lines used for drawing polygonal lines. Similarly, i refers to a coordinate line in the i position of the horizontal coordinate line I, and j refers to a coordinate line in the j position of the vertical coordinate line J. As is shown in FIG. 7, the horizontal coordinate lines i are given such numbers as "0" to "Imax−1" from the top of the screen 13 downward, while the vertical coordinate lines J are given such numbers as "0" to "Jmax-1" from left to right. Under such definitions, the positional coordinate of the lattice point 25 is expressed by (i, j).

First, a mouse is moved, while depressing a left button of the mouse, to encircle a desired area. Then, the left button of the mouse is depressed to set the increment "n" to n=0. At that time, the coordinate of the point 25 designated by a cursor is set to (i0, j0) as shown in FIG. 5. This coordinate (i0, j0) is stored in the locus arrangement memories Li0[0] and Lj0[0]. They are expressed by Li0[0]=i0 and Lj0[0]=j0 here.

Next, it is presumed that the mouse is operated to bring the tip of the cursor 26 to a different lattice point 25' from the coordinate (i0, j0). When a distance L between the lattice point 25' where the tip of the cursor 26 is currently located and the lattice point 25 previously designated by the cursor 26 reaches a predetermined value or more, the locus arrangement memory index "n" is incremented. One increment corresponds to one straight line drawn. At the same time, in this case, the coordinate (i1, j1) of the lattice point 25' currently designated by the cursor 26 is stored in the locus arrangement memories Li[1] and Lj[1]. By this, the computer connects the lattice points 25 and 25' by a straight line and displays the straight line on the screen 13. The reason to pick up the points, which are away from each other by a predetermined distance or more, is as follows. If a straight line is to be drawn by pitch unit of lattice points, the amount of memory required is remarkably increased. Since this is not practical, it is attempted to save memory. In this embodiment, in order to perform an arithmetic operation simply, instead of calculating an absolute value between the previous point 25 and the current point 25', the lattice point is sampled when the sum of a horizontal pitch $\Delta j$ of the lattice point and a vertical pitch $\Delta i$ thereof is a predetermined value or more. In the example shown in FIG. 5, it is presumed that the sample point is obtained when the total is 6 pitches or more. In accordance with the movement of this mouse, the operation is performed until a desired closed curve is drawn. Presuming that a polygonal line in the m position is processed when the left button of the mouse is released, the computer proceeds with the operation considering that the locus arrangement memory Li[m] and the locus arrangement memory Li[0] are same, and that the locus arrangement memory Lj[0] and the locus arrangement memory Lj[m] are same. In FIG. 5, since the polygonal line is formed of eight straight lines, m=8. Accordingly, the mouse acts as a part of the boundary designating means for designating the adding or deleting area of the inspecting points by connecting various points so that a closed curve is drawn on the screen 13.

It is presumed that straight lines forming the polygonal lines as shown in FIG. 5 are obtained in this way. Next, when the right button of the mouse is depressed, the computer effects interpolation with respect to each side and finds the coordinate values of points of intersection between the total coordinate lines of (i, j) intersecting with the closed curve, and the closed curve. Furthermore, the computer finds a maximum coordinate value and a minimum coordinate value at the total coordinate lines of (i, j) from the coordinate values of the points of intersection between the total coordinate values of (i, j) and the closed curve and stores them in the area limit arrangement memory. As the area limit arrangement memory, the followings are prepared.

That is, imin[j], imax[j], jmin[i], and jmax[i] are prepared. imin[j] refers to a minimum value of i on the vertical coordinate line, imax[j] refers to a maximum value of i on the vertical coordinate line, jmin[i] refers to a minimum value of j on the horizontal coordinate line, and jmax[i] refers to a maximum value of j on the horizontal coordinate line. In the foregoing, i is an integer from 0 to Imax−1 and j is an integer from 0 to Jmax−1.

There are two methods here for storing the maximum coordinate value and the minimum coordinate value at the total coordinate lines of respective i, j in the area limit arrangement memory. In the first method, the computer temporarily memorizes the coordinate values of the points of intersection interpolated, and then finds a maximum coordinate value and a minimum coordinate value from the coordinate values of such memorized points of intersection, and then stores them in the area limit arrangement memory. In the second method, each time the computer obtains a coordinate value of a point of intersection interpolated, it compares the value with data already stored in the area limit arrangement memory and replaces the value with a maximum coordinate value and a minimum coordinate value stored whenever the maximum coordinate value and the minimum coordinate value are obtained.

Figure 8:
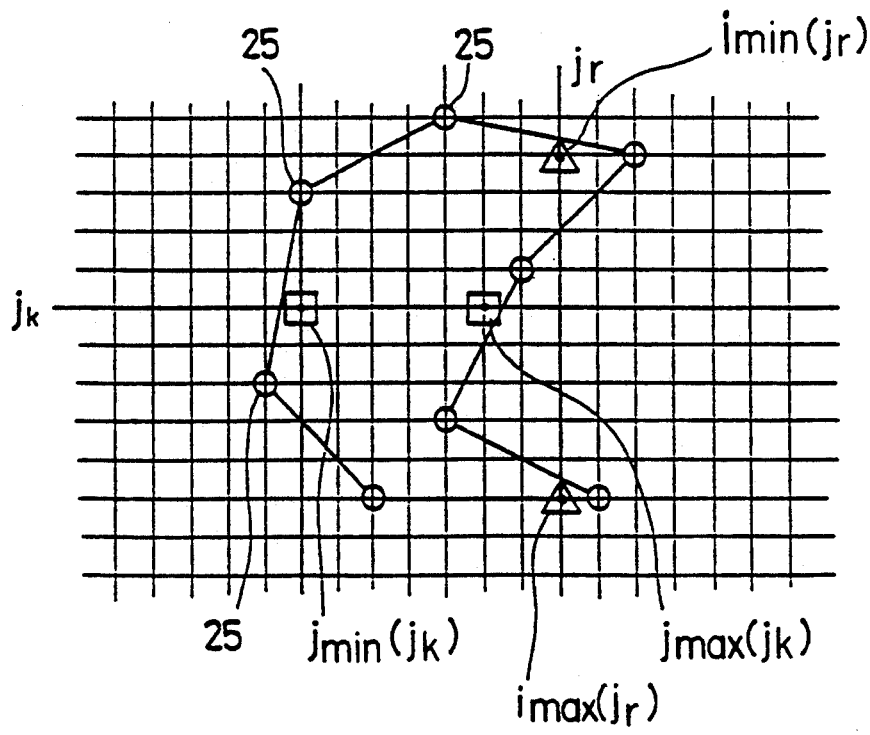
FIG. 8 is a view for designating an adding or deleting area of the inspecting points based on an XY pattern.

The number n of the straight lines forming the polygonal lines is now presumed to be np=8, and the sample point (Li[n], Lj[n]) and the sample point (Li[n+1], Lj[n+1]) are connected to interpolate a term in a series of straight lines with respect to a number of from n=0 to n=np−1. For example, as is shown in FIG. 8, a point of interpolation on the horizontal coordinate line in (i, k) position between the sample point (Li[1], Lj[1]) and the sample point (Li[2], Lj[2]) are obtained as jmin[ik], jmax[ik] as encircled by □, while a point of interpolation on the vertical coordinate line in (j, r) position is obtained as imin(j, r), imax(j, r) as encircled by Δ. In this way, maximum and minimum collections of the area limit arrangement which is most fitted to the closed curve formed of polygonal lines are made. And with respect to all lattice points, it is judged whether or not the coordinate (i, j) satisfies the conditions set forth below.

$$imin[j] \leq i \leq imax[j]$$

and $$jmin[i] \leq i \leq jmax[i]$$

By executing this processing, lattice points 25 belonging to the adding or deleting area of the inspecting points are distinguished from the lattice points 25 which do not belong thereto. And they are stored in a register arrangement memory ip[], jp[] for determining as inspecting points corresponding to target marks to be exhibited. If the lattice point of the coordinate (i, j) is an inspecting point within the area, ip[n]=i and jp[n]=j. This operation is repeated with respect to n from n=0 to np.

The target mark corresponding to the lattice point stored in this register arrangement memory is to be exhibited or deleted. Accordingly, the computer acts as exhibiting target mark determining means for determining a target mark which is to be exhibited on the target mark exhibiting means based on the adding or deleting area of the inspecting point predetermined by the boundary designating means.

After determining the range of target marks to be exhibited, the computer cancels the interruption (S13). And the measuring procedure is resumed (S4). By this, target marks are exhibited one after another on the inner surface 10 of the dome 3.

Next, there will be described a case where the adding or deleting area of the inspecting points is designated using the MO coordinate pattern.

Figure 9:
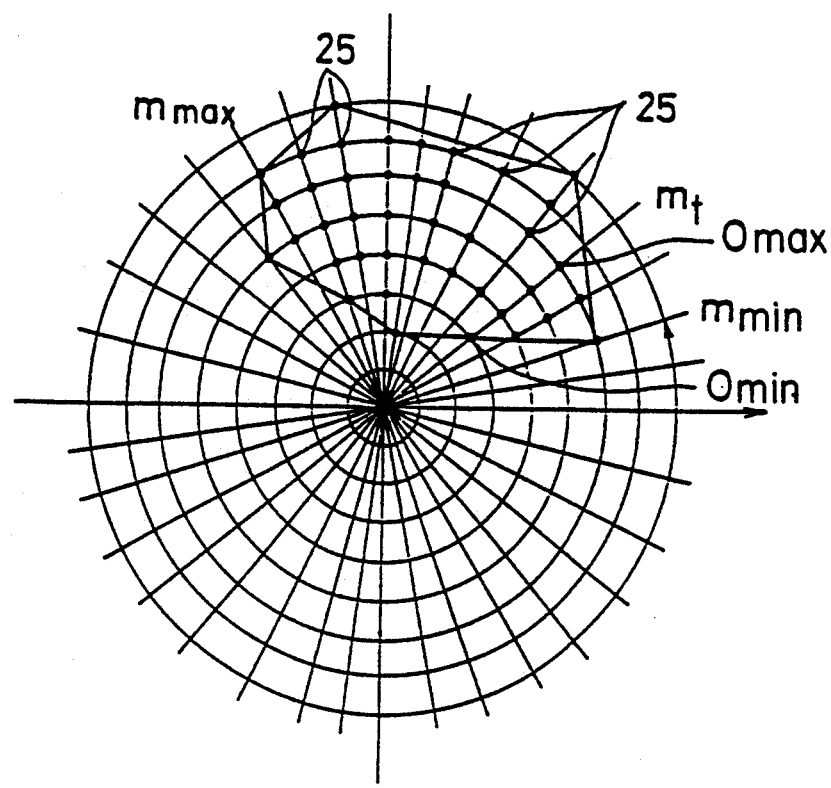
FIGS. 9 and 10 are views for designating an adding or deleting area of the inspecting points based on an MO pattern respectively.
Figure 10:
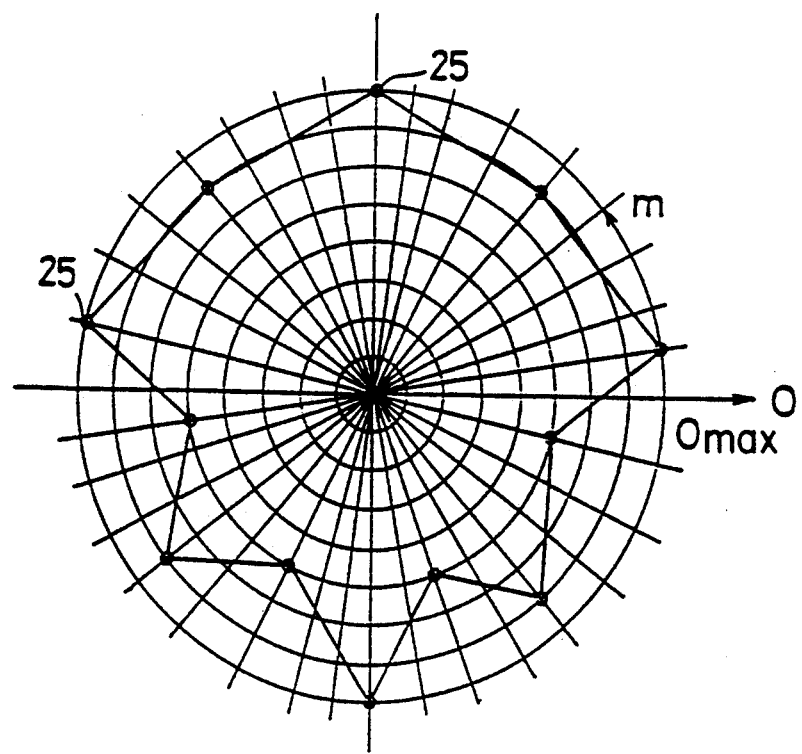

In this case, as is shown in FIG. 9, the lattice points 25 are located within each of the angular direction coordinate lines within the angular direction coordinate lines m(min), m(max). Then, O(min), O(max) of the radial direction coordinate lines are found with respect to each of the angular direction coordinate lines, and the lattice points located within the Omin, Omax are found. For example, in the case of angular direction coordinate mt, Omin, Omax are found with respect to the angular direction coordinate line mt and then the lattice points located within these Omin, Omax are found. By the way, in case the origin is encircled as shown in FIG. 10, a false Omin appears. However, in this case, it may simply designate Omin=0.

Although several embodiments have been described, the present invention includes the followings.

① The automatic perimeter includes those which exhibit target marks using an LED.

② A closed curve temporarily set can be deleted and changed using a mouse.

③ In this embodiment, although the lattice points located within the adding or deleting area of the inspecting points are designated as inspecting points, the lattice points located outside the adding or deleting area can be designated as the inspecting points.

④ When several lattice points, which are not intended to be measured, are included within the adding or deleting area of the inspecting points, such several lattice points can be deleted individually using a mouse.

What is claimed is:

1. An automatic perimeter for measuring the field of vision of a patient, comprising:
    target mark exhibiting means for exhibiting a target mark at an inspecting point having a predetermined position, in accordance with instructions from an instructing means;
    display means having a screen for displaying points on the screen corresponding, one by one, to the inspecting points to be exhibited by said target mark exhibiting means;
    boundary designating means for designating an adding or deleting area of the inspecting points by drawing a closed curve on the screen of said display means; and
    exhibiting target mark determining means for determining the inspecting points to be exhibited by said target mark exhibiting means based on the adding or deleting area of the inspecting points determined by said boundary designating means;
    said instructing means instructing said target mark exhibiting means to exhibit the target marks determined by said exhibiting target mark determining means.

2. An automatic perimeter as claimed in claim 1, wherein said target marks are exhibited by said target mark exhibiting means in an optional order.

3. An automatic perimeter as claimed in claim 2, wherein said target mark exhibiting means includes a dome, target mark spot light emitting means for emitting a target mark spot light, and a target mark projecting mechanism for reflecting said target mark spot light and guiding said target mark spot light into a predetermined position on an inner surface of said dome in accordance with instructions from said instructing means.

4. An automatic perimeter as claimed in claim 2, wherein said display means includes means for displaying thereon target marks in such a manner that target marks which have been exhibited can be distinguished from those which have not yet been exhibited.

5. An automatic perimeter as claimed in claim 2, which further includes means for changing a pitch of the points to be displayed on the screen of said display means corresponding, one by one, to the inspecting points to be exhibited on said target mark exhibiting means.

6. An automatic perimeter as claimed in claim 2, wherein said display means displays thereon a lattice coordinate pattern for adding or deleting the inspecting points, and said boundary designating means designates the adding or deleting area of the inspecting points by drawing a closed curve by connecting lattice points by polygonal lines.

7. An automatic perimeter as claimed in claim 6, wherein a distance between the lattice points connected by the polygonal lines is greater than or equal to a predetermined value.

8. An automatic perimeter as claimed in claim 6, wherein said lattice coordinate pattern is a vertical and horizontal pattern, and a distance between the lattice points connected by the polygonal lines can be designated by assuming a horizontal pitch and a vertical pitch of the lattice points.

9. A method for measuring the field of vision of a patient using an automatic perimeter, comprising:
    selecting an inspection pattern having a plurality of inspecting points;
    displaying points corresponding to said inspecting points on a screen of a display device of said automatic perimeter;
    designating an area of said inspection pattern from which inspecting points are added or deleted from said inspection pattern by drawing a closed curve on said screen of said display device;
    determining the inspecting points to be exhibited to the patient based on the area determined by said closed curve in said designating step; and
    exhibiting target marks to the patient at the inspecting points determined in said determining step.

10. A method as claimed in claim 9, wherein said target marks are exhibited in an optional order.

11. A method as claimed in claim 10, further comprising the steps of:
    emitting a target mark spot light from said automatic perimeter;
    reflecting said target mark spot light and guiding said target spot light into a predetermined position on an inner surface of a dome of said automatic perimeter in accordance with instructions from said automatic perimeter.

12. A method as claimed in claim 10, wherein said inspecting points are displayed on said screen of said display device in such a manner that inspecting points which have been exhibited as target marks in said exhibiting step can be distinguished from those which have not yet been exhibited.

13. A method as claimed in claim 10, further comprising the step of changing a pitch of the points to be displayed on the screen of said display means.

14. A method as claimed in claim 10, wherein said displaying step includes displaying a lattice coordinate pattern for adding or deleting said inspection points on said screen of said display device, and said designating step includes designating the area of the inspection pattern from which inspecting points are to be added or deleted by drawing a closed curve by connecting lattice points by polygonal lines.

15. A method as claimed in claim 14, wherein a distance between the lattice points connected by said polygonal lines is greater than or equal to a predetermined value.

16. A method as claimed in claim 14, wherein said lattice coordinate pattern has horizontal and vertical coordinates.

17. A method as claimed in claim 16, further comprising the step of sampling the lattice points connected by polygonal lines by calculating a distance between said lattice points by summing a horizontal pitch and a vertical pitch of said lattice points.

* * * * *